US00PP17370P3

(12) United States Plant Patent

Cave et al.

(10) Patent No.: US PP17,370 P3
(45) Date of Patent: Jan. 16, 2007

(54) *ERYNGIUM PLANUM* PLANT NAMED 'JADE FROST'

(50) Latin Name: *Eryngium planum*
Varietal Denomination: Jade Frost

(76) Inventors: James Andrew Cave, 57 Gwarth an Drae, Helston Cornwall TR13 0BS (GB); Megan Kathryn Cave, 57 Gwarth an Drae, Helston Cornwall TR13 0BS (GB)

( * ) Notice: Subject to any disclaimer, the term of this patent is extended or adjusted under 35 U.S.C. 154(b) by 0 days.

(21) Appl. No.: 11/225,300

(22) Filed: Sep. 12, 2005

(65) Prior Publication Data

US 2006/0130207 P1 Jun. 15, 2006

(51) Int. Cl.
*A01H 5/00* (2006.01)

(52) U.S. Cl. ..... Plt./361

(58) Field of Classification Search ..... Plt./361
See application file for complete search history.

(56) References Cited

U.S. PATENT DOCUMENTS

PP7,152 P * 2/1990 Vletter ..... Plt./361

* cited by examiner

*Primary Examiner*—Kent Bell
*Assistant Examiner*—June Hwu
(74) *Attorney, Agent, or Firm*—Klarquist Sparkman LLP

(57) ABSTRACT

A new and distinct *Eryngium planum* plant characterized by blue green leaves with prominent white margins, new leaves with pink edges in cool night temperatures, violet blue-colored flowers and flowering stem branches, and excellent vigor.

1 Drawing Sheet

Botanical denomination: *Eryngium planum.*
Variety designation: 'Jade Frost'.

The present invention relates to a new and distinct cultivar of *Eryngium planum,* and given the cultivar name 'Jade Frost'. *Eryngium* is in the family Apiaceae.

This new cultivar originated as a sport of green leaf *Eryngium planum* planted in a cultivated area.

This new *Eryngium* cultivar has unique variegated leaves. It is the only variegated form of *Eryngium planum* known to the breeder.

This plant is characterized by the following:

1. White edged mature leaves and bracts. (Main leaf color is blue green.)
2. New leaves are pink edged in cool nights (when grown below 45 degrees F.).
3. Violet blue-colored flowers and flowering stem branches.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of a one year old *Eryngium* 'Jade Frost' grown in the ground in full sun in the trial field in Canby, Oreg.

DETAILED PLANT DESCRIPTION

The following is a detailed description of the new *Eryngium planum* based on observations of one-year-old specimens growing in the ground in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Hardiness.*—USDA Zones 5 to 9.
*Size.*—Foliage grows to 35 cm wide and 16 cm tall and height is 80 cm tall to top of flowers.
*Form.*—Basal clump.
*Vigor.*—Excellent.
*Roots.*—Thick, fibrous, Greyed Brown 199D, plants may be propagated crown divisions or tissue culture.

Basal leaves:

*Type.*—Simple.
*Shape.*—Oblong to oblong ovate.
*Arrangement.*—Rosette.
*Blade length.*—Grows to 12 cm.
*Width.*—Grows to 6 cm.
*Margins.*—Serrate.
*Apex.*—Acute.
*Base.*—Cordate.
*Surface texture.*—Glabrous, slightly leathery.
*Venation.*—Pinnate.
*Color.*—Topside — center Greyed Green 189A with creamy white margins, Yellow White 158A, with an occasional transitional area between the center and the margin colored Greyed Green 189B, creamy margins pink in cool temperatures, Greyed Purple 186C. Bottom — same as above.

*Petiole description.*—Grows to 9 cm long and 6 mm wide, glabrous on both sides, Green 138A on bottom side and top side Green 138A with stripes of pink, Greyed Purple 186D.

Inflorescence:

*Type.*—A loose candelabriform raceme.

*Raceme size* (*excluding stalk*).—28 cm wide and 66 cm high.

*Number of panicles per crown.*—1.

*Flower number.*—Count of 130 flowers on one panicle.

*Peduncle description.*—Type — ascending. Size — grows to 53 cm tall and 15 mm wide. Internode length — 3 to 7 cm. Surface texture — glabrous. Color — Violet Blue 92A to 92C with Yellow Green 146D near the base. Cauline leaves — about 15, ovate (upper leaves palmatifid), serrate, glabrous, color same as basal leaves, grow to 11.5 cm long and 6 cm wide, sessile and clasping except near base where they are 4 cm long and grow to 1 cm wide. Color — in horizontal stripes up the stem, the bottom half is Yellow White 158D and Greyed Green 195A, the top half is Violet Blue 92A. Branching — glabrous, Violet Blue 92A.

*Fragrance.*—None.

*Bloom time.*—August to September in Canby, Oreg.

Capitulum bud:

*Size.*—10 mm wide and 14 mm deep.

*Description.*—Conical, subtended by bracts.

*Surface.*—Spiny.

*Color.*—White 155A with subtending bracts closest to Violet Blue 94A on top and bottom side Greyed Green 189A with slight Yellow White 158A on the margins.

Flower:

*Type.*—Perfect, complete, regular, congested in a capitulum with spiny involucral bracts.

*Size.*—2.5 mm wide and 6 mm deep including stamens.

*Color.*—Violet Blue 91A.

*Corolla.*—5 petals, 2 mm long, entire, Violet Blue 91A at tips and White 155A at base.

*Calyx.*—5 sepals, emarginate, 3 mm long, Violet Blue 91A at tips and White 155A at base.

*Stamens.*—5, filaments 2.5 mm long, filaments and anthers Violet Blue 91A, pollen White 155D.

*Pistil.*—Stigma and style Violet Blue 91A, style 4 mm long, ovary 3 mm long, Yellow Green 145A and covered with tubercles, White 155A.

Capitulum: Range in size from 1.5 cm long when flowers first opening to 2.3 cm long when flowers are mature, 1.4 cm wide, Violet Blue 92A, subtended by usually 9 involucral bracts which grow to 2.2 cm long and 3 mm wide, lanceolate, entire, cupped, each with spiny tip and 0 to 3 lateral spines, glabrous, Violet Blue 94A on top side and bottom side Greyed Green 189A with mottled Yellow White 158A on the margins.

Fruit: Is the dried capitulum, oval, 2.3 cm long and 1.9 cm wide, Greyed Green 197A.

Seed:

*Color.*—Grey Brown 199A.

*Size.*—Approximately 1 mm. long.

*Shape.*—Oval.

*Fertility.*—Fertile.

Disease and pests: *Eryngium* are prone to root rot and should be planted in dry, well drained, poor to moderately fertile soil in full sun. Slugs, snails, and powdery mildew are also known problems. No known resistance.

Comparisons: Compared to its parent *Eryngium planum,* the new variety has a bluer leaf color that is also variegated leaf instead of an all green leaf.

Compared to *Eryngium planum* 'Calypso' (U.S. Plant Pat. No. 7,152), the new variety has foliage that is more blue in color and its young leaves turn pink on the variegated part in the cool night temperatures of spring and fall.

I claim:

1. A new and distinct *Eryngium planum* plant as herein illustrated and described.

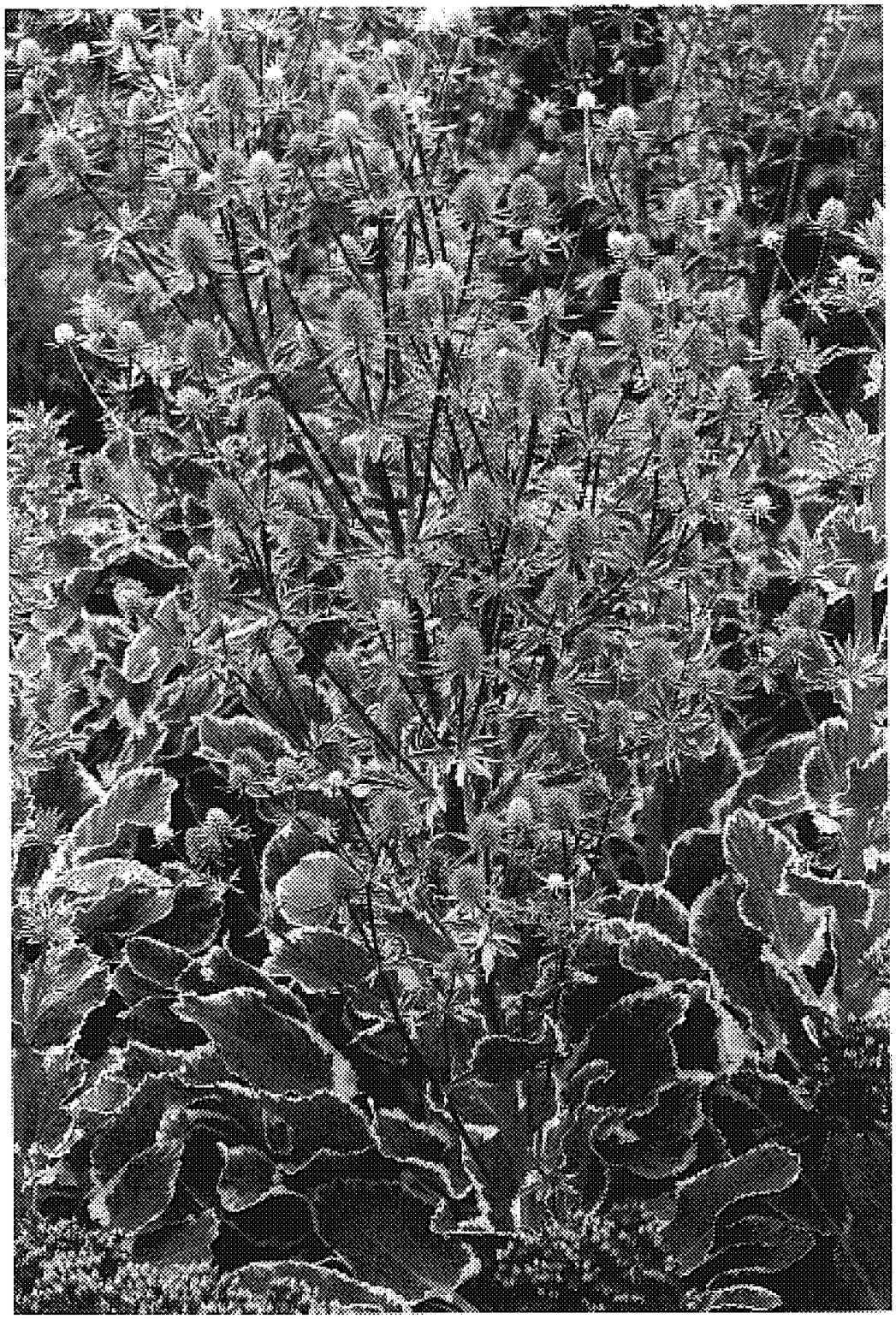

* * * * *